(12) United States Patent
Pudduck

(10) Patent No.: US 12,318,784 B2
(45) Date of Patent: Jun. 3, 2025

(54) FITMENT DEVICES, REAGENT CARTRIDGES, AND METHODS THEREOF

(71) Applicant: Siemens Healthcare Diagnostics Inc., Tarrytown, NY (US)

(72) Inventor: Christian Pudduck, Norfolk, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 6 days.

(21) Appl. No.: 17/593,318

(22) PCT Filed: Mar. 12, 2020

(86) PCT No.: PCT/US2020/022329
§ 371 (c)(1),
(2) Date: Sep. 15, 2021

(87) PCT Pub. No.: WO2020/190633
PCT Pub. Date: Sep. 24, 2020

(65) Prior Publication Data
US 2022/0193679 A1      Jun. 23, 2022

Related U.S. Application Data

(60) Provisional application No. 62/821,626, filed on Mar. 21, 2019.

(51) Int. Cl.
*B01L 3/00* (2006.01)
*B65D 75/58* (2006.01)
*G01N 35/00* (2006.01)

(52) U.S. Cl.
CPC .......... *B01L 3/523* (2013.01); *B65D 75/5883* (2013.01); *G01N 35/00693* (2013.01);
(Continued)

(58) Field of Classification Search
CPC .............. B01L 3/523; B01L 2200/026; B01L 2200/0689; B01L 2300/123;
(Continued)

(56) References Cited

U.S. PATENT DOCUMENTS 5,390,814 A    2/1995  Christine et al.
5,665,315 A    9/1997  Robert et al.
(Continued)

FOREIGN PATENT DOCUMENTS

EP    0255210 A2    2/1988
EP    0414992 A1    3/1991
(Continued)

OTHER PUBLICATIONS

Keller et al., "Water Vapor Premeation in Plastics", USDOE, Dept. of Homeland Security (DHS) (United States), Jan. 1, 2017, Revision 1, pp. 1-37.
(Continued)

*Primary Examiner* — Samuel P Siefke

(57) ABSTRACT

A fitment device may include a core made of a first material and including a securing portion configured to secure to a chassis and a container portion configured to seal to a container. The fitment device includes an aperture including a first end located at the securing portion and a second end located at the container portion, wherein the aperture is configured to receive a probe in the first end. A plug located in the aperture is movable within the aperture upon contact with the probe to open a passageway between the first end and an interior of the container. Other devices and methods are disclosed.

21 Claims, 8 Drawing Sheets

(52) U.S. Cl.
CPC . *B01L 2200/026* (2013.01); *B01L 2200/0689* (2013.01); *B01L 2300/123* (2013.01); *B01L 2400/0633* (2013.01)

(58) Field of Classification Search
CPC ........ B01L 2400/0633; B65D 75/5883; G01N 35/00693; G01N 33/4925
See application file for complete search history.

(56) References Cited

U.S. PATENT DOCUMENTS

| | | | |
|---|---|---|---|
| 5,882,602 A | 3/1999 | Savage et al. | |
| 5,913,232 A | 6/1999 | Betts et al. | |
| 5,918,777 A | 7/1999 | Flak | |
| 8,191,735 B2 | 6/2012 | Laible | |
| 8,276,793 B2 | 10/2012 | Dicks et al. | |
| 2002/0066712 A1 | 6/2002 | Brockwell | |
| 2002/0166394 A1 | 11/2002 | Mathur et al. | |
| 2003/0047467 A1 | 3/2003 | Smith et al. | |
| 2004/0076546 A1 | 4/2004 | Bissett | |
| 2005/0150917 A1* | 7/2005 | Dicks ................ B29C 66/72341 222/566 | |
| 2007/0272710 A1 | 11/2007 | Bui | |
| 2010/0213215 A1* | 8/2010 | Laible ...................... B67D 7/36 222/518 | |
| 2015/0125574 A1 | 5/2015 | Arent et al. | |
| 2015/0210458 A1 | 7/2015 | Ziegenfelder et al. | |
| 2015/0355207 A1 | 12/2015 | Pollack et al. | |
| 2015/0361488 A1 | 12/2015 | Schultz et al. | |
| 2016/0184826 A1 | 6/2016 | Nemoto et al. | |
| 2016/0242674 A1 | 8/2016 | Ahmad et al. | |
| 2017/0266664 A1 | 9/2017 | Lukhaub et al. | |
| 2018/0043363 A1 | 2/2018 | Blankenstein et al. | |
| 2018/0290141 A1 | 10/2018 | Knight | |
| 2019/0344258 A1* | 11/2019 | Motadel ................ B01L 3/0275 | |

FOREIGN PATENT DOCUMENTS

| | | |
|---|---|---|
| EP | 1396439 A1 | 3/2004 |
| JP | S63170035 A | 7/1988 |
| JP | 10288664 A | 3/1990 |
| JP | H10185776 A | 7/1998 |
| JP | H11133032 A | 5/1999 |
| JP | 2001509047 A | 7/2001 |
| JP | 2008094454 A | 4/2008 |
| JP | 2012021861 A | 2/2012 |
| JP | 2017181033 A | 10/2017 |
| WO | 9744662 A1 | 11/1997 |
| WO | 0063080 A2 | 10/2000 |
| WO | 2018184902 A1 | 10/2018 |

OTHER PUBLICATIONS

International Search Report and Written Opinion of International Application No. PCT/US2020/022329 dated Jun. 12, 2020.

\* cited by examiner

FITMENT DEVICES, REAGENT CARTRIDGES, AND METHODS THEREOF

This application claims priority to U.S. Provisional Application No. 62/821,626, filed Mar. 21, 2019, the disclosure of which is incorporated herein by reference in its entirety.

FIELD

The present application relates to gas analyzers and more particularly to fitment devices, reagent containers, reagent cartridges, and methods of using and manufacturing thereof.

BACKGROUND

Gas analyzers, such as blood gas analyzers, undergo frequent calibration to maximize analyzer accuracy due to analyzer results drift, such as due to temperature and the like. Calibrated reagents can be supplied as reagent pouches to the gas analyzers and the contents thereof are analyzed to calibrate the gas analyzers. In order to provide accurate calibration, the calibration reagents should be pure.

Accordingly, improved calibration reagent and gas analyzer calibration methods are sought.

SUMMARY

In some embodiments, fitment devices are provided. The fitment devices may include: a core comprising a first material and including a securing portion configured to secure to a chassis and a container portion configured to seal to a container, an aperture comprising a first end located at the securing portion and a second end located at the container portion, the aperture configured to receive a probe in the first end, and a plug located in the aperture, wherein the plug is movable in the aperture upon contact with the probe to open a passageway between the first end and the second end.

In other embodiments, reagent cartridges are provided. The reagent cartridges include at least one pouch assembly configured to hold a reagent, the at least one pouch assembly further comprising: a fitment device comprising a first material and including a securing portion configured to secure to a chassis and a container portion sealed to a container of the pouch assembly, an aperture including a first end located at the securing portion and a second end located at the container portion, and a plug located in the aperture; and at least one probe having a first position where the at least one probe is spaced from the first end of the aperture and a second position where the at least one probe is received in the first end of the aperture, wherein the at least one probe is configured to move the plug in the aperture in response to the at least one probe being in the second position to open a passageway between the first end and the container.

In other embodiments, pouch assemblies are provided. The pouch assemblies include a container; and a fitment device coupled to the container, the fitment device further comprising: a core comprising a first material and including a securing portion configured to secure to a chassis, and a container portion configured to seal to the container; an aperture comprising a first end located at the securing portion and a second end located at the container portion, the aperture configured to receive a probe in the first end; and a plug located in the aperture, wherein the plug is movable in the aperture upon contact with the probe to open a passageway between the first end and the container.

In some embodiments, methods of using a reagent cartridge are disclosed. The methods may include providing a reagent cartridge comprising: a fitment device comprising a first material and including a securing portion secured to a chassis and a container portion sealed to a container, an aperture extending between a first end located at the securing portion and a second end located at the container portion, and a plug located in the aperture; moving a probe into the first end of the aperture and pushing the plug with the probe in response to moving the probe into the first end of the aperture to open a passageway between the first end and an interior of the container.

Numerous other aspects and features are provided in accordance with these and other embodiments of the disclosure. Other features and aspects of embodiments of the disclosure will become more fully apparent from the following detailed description, the claims, and the accompanying drawings.

BRIEF DESCRIPTION OF DRAWINGS

The drawings, described below, are for illustrative purposes only and are not necessarily drawn to scale. The drawings are not intended to limit the scope of the disclosure in any way. Wherever possible, the same or like reference numbers will be used throughout the drawings to refer to the same or like parts.

DETAILED DESCRIPTION

Figure 1A:
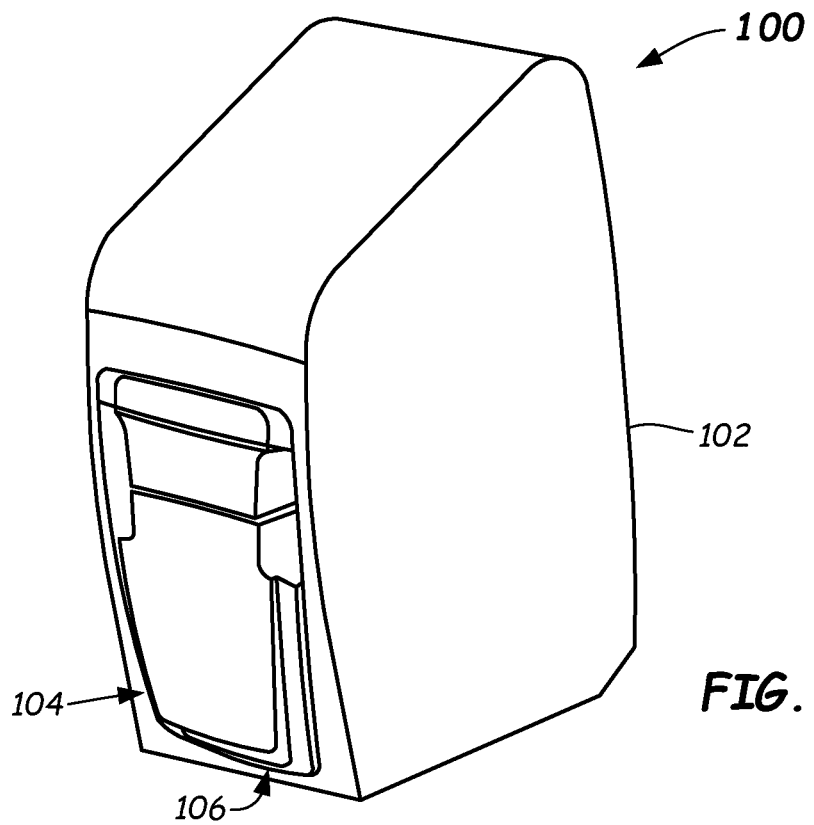
FIG. 1A illustrates a side isometric view of a gas analyzer in a closed state according to embodiments disclosed herein.

Reference will now be made in detail to the example embodiments provided, which are illustrated in the accompanying drawings. Features of the various embodiments described herein may be combined with each other unless specifically noted otherwise.

Gas analyzers, such as blood gas analyzers, undergo frequent calibration in order to provide accurate analysis and test results. For example, calibration may be performed at a start of a testing sequence, after a testing sequence, or even before and after a testing sequence. For maximum effectiveness, it is desired that the calibration reagents are not contaminated by external gases, such as oxygen. This is especially true for blood gas testing, for example. Conventional pouch assemblies that store the calibration reagents may, in some instances, be somewhat permeable to gas, which can degrades the calibration reagents and may contribute to less accurate calibration.

Pouch assemblies filled with certain calibration reagents may be supplied to the gas analyzers. The calibration reagents include known and precise chemical compositions that are analyzed by the gas analyzers. For example, the gas analyzers may analyze dissolved oxygen, carbon dioxide, and other chemicals in the calibration reagents. The results of the analysis of the calibration reagents can be used by the gas analyzers for their calibration, i.e., adjustment thereof.

The pouch assemblies may include containers that store the calibration reagents, and fitment devices to enable the gas analyzers to access the calibration reagents and to secure the pouch assemblies within the gas analyzers. These conventional fitment devices may have a gas permeability that is high enough to allow gas into and out of the containers, which can degrade the calibration reagents. The degraded calibration reagents can thus cause inaccurate calibration and thus can cause some inaccuracies in the gas analysis.

Pouch assemblies, containers, fitment devices, and other apparatus having low gas permeability are disclosed herein and are described with reference to FIGS. 1A-6. The pouch assembly embodiments described herein may each include a fitment device that secures the pouch assembly to a reagent cartridge and also enables access to a reagent (e.g., a calibration reagent) stored in a container coupled to the fitment device. The fitment device may include a securing portion that is configured to secure the pouch assembly to a chassis or the like within a reagent cartridge. The fitment device may also include a container portion that seals the fitment device to the container. An aperture may extend between the securing portion and the container portion. A moveable plug may be located in the aperture and may seal the aperture so as to prevent the flow of gases through the aperture, such as when is storage. In use, a probe, that can be part of a reagent cartridge, may be receivable in the aperture and may push the plug from the aperture to enable the gas analyzer to access the calibration reagent.

The fitment device may include a core made from a first material, such as nylon, that has low gas (e.g., oxygen) permeability. The plug may be made from a second material that also has low gas (e.g., oxygen) permeability. The plug may be flexible. The flexibility of the plug enables the plug to seal to the aperture of the fitment device. To gain access to the reagent, the plug is pushed from the aperture by the probe. The disclosed configuration of the fitment device reduces the gas permeability of the pouch assembly, which helps to preserve, i.e., minimize gas contamination of, the reagent located therein. Fitment devices, pouch assemblies, and other apparatus and methods disclosed herein may be used in other devices and with other liquids.

Figure 1B:
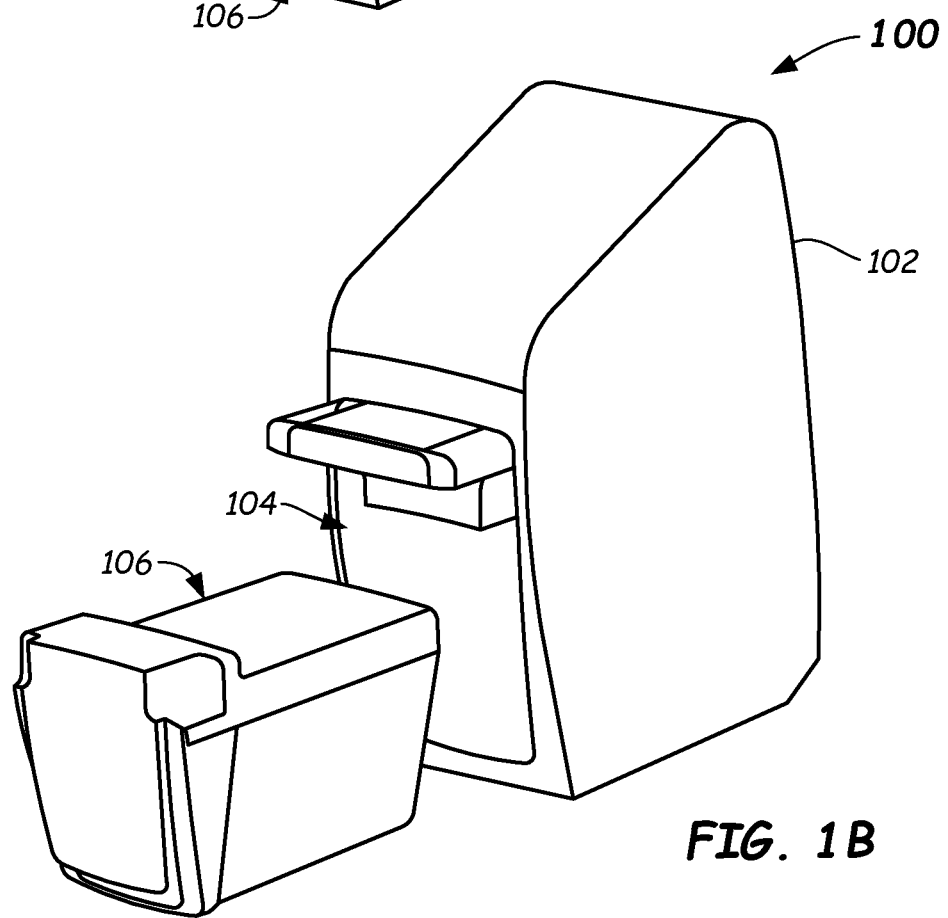
FIG. 1B illustrates a side isometric view of a gas analyzer in an open state and receiving or removing a reagent cartridge therein according to embodiments disclosed herein.

Reference is now made to FIG. 1A, which illustrates a side isometric view of a gas analyzer 100 (e.g., a blood gas analyzer) shown in a closed state. Reference is also made to FIG. 1B, which illustrates the gas analyzer 100 in an open state. The gas analyzer 100 may, in some embodiments, analyze liquid samples (e.g., whole blood or blood plasma or serum) and may measure a concentration level of one or more chemicals or constituents in the samples, such as a concentration of a gas therein. The gas analyzer 100 may include a body 102 including an opening 104, wherein a removable reagent cartridge 106 may be receivable in the opening 104. FIG. 1A illustrates the gas analyzer 100 in the closed state wherein the reagent cartridge 106 is received within the opening 104. FIG. 1B illustrates the gas analyzer 100 in the open state wherein the reagent cartridge 106 is removed from the opening 104. Other manners for engaging the reagent cartridge 106 with the analyzer can be used.

The reagent cartridge 106 may include a plurality of calibration reagents (e.g., liquid calibration reagents) stored in a plurality of pouches (not shown in FIG. 1A or 1B). The calibration reagents may be stored in individual containers and may contain precise levels of dissolved gases used by the gas analyzer 100 for calibration. For example, the gas analyzer 100 may analyze the calibration reagents and determine that specific chemicals (e.g., gases) are present in the calibration reagents. The gas analyzer 100 may then be calibrated based on the differences between the analysis and the specific chemicals known to be in the calibration reagents.

Figure 2A:
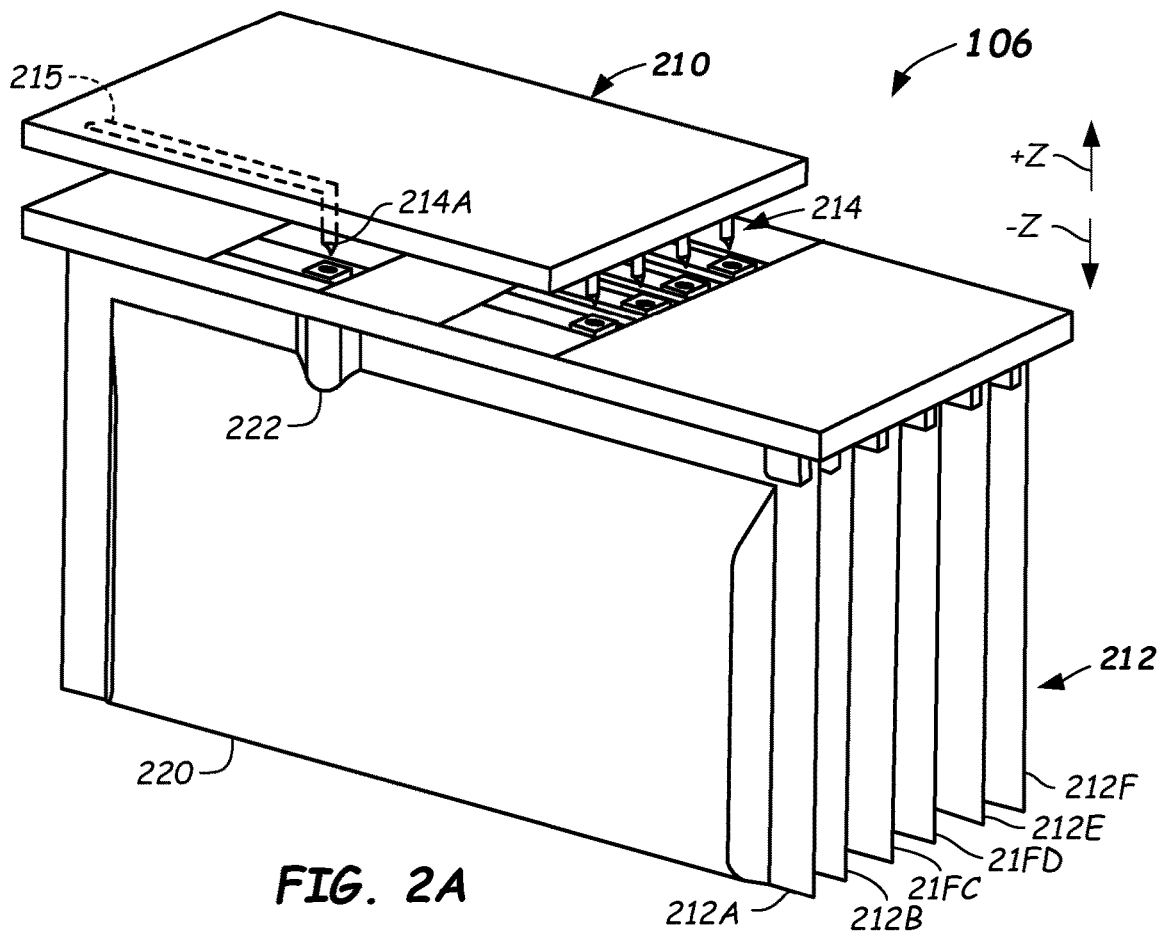
FIG. 2A illustrates an isometric view of an interior of a reagent cartridge configured to be used in a gas analyzer according to embodiments disclosed herein.
Figure 2B:
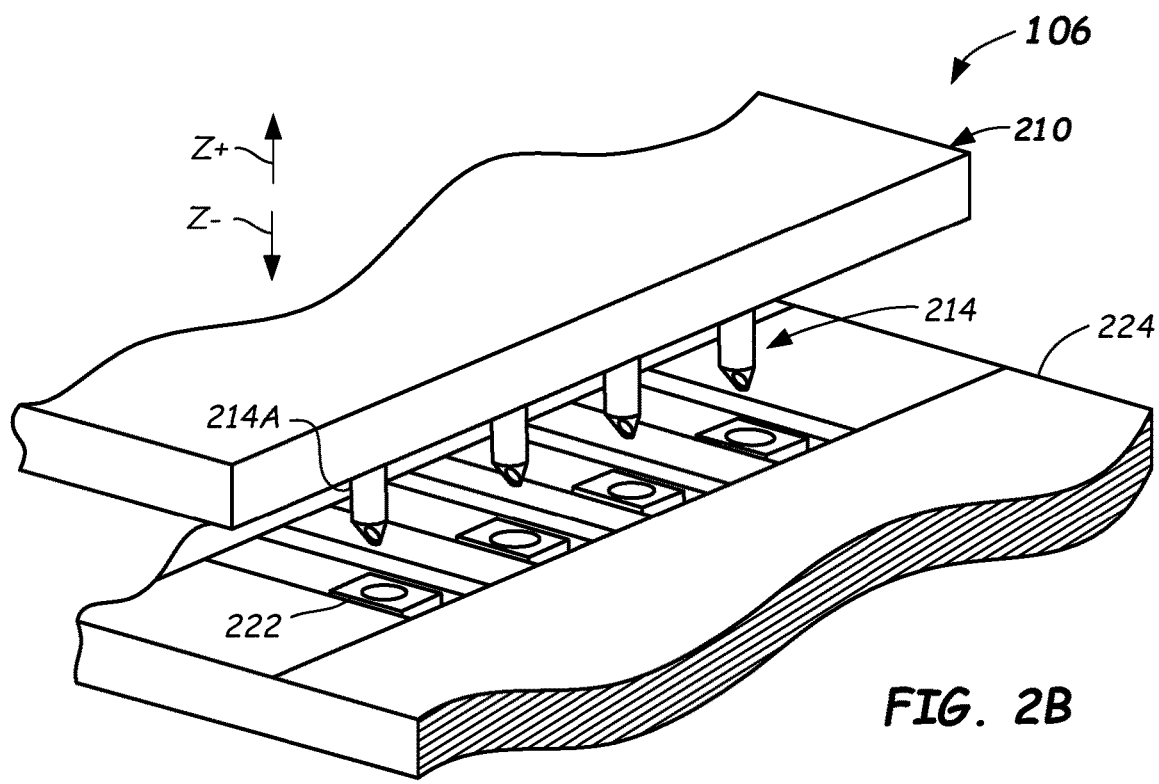
FIG. 2B illustrates an enlarged partial view of a manifold and other components within a reagent cartridge according to embodiments disclosed herein.

Reference is now made to FIG. 2A, which illustrates an example of the interior of the reagent cartridge 106. Reference is also made to FIG. 2B, which illustrates an enlarged view of a manifold 210 and other components within the reagent cartridge 106. The reagent cartridge 106 may include a plurality of pouch assemblies 212 (e.g., reagent pouch assemblies) that are configured to store the calibration reagents. The embodiment of the reagent cartridge 106 illustrated in FIG. 2A shows six pouch assemblies 212 referred to individually as pouch assemblies 212A-212F. The reagent cartridge 106 may include other numbers of pouch assemblies. A plurality of probes 214 may be coupled to the manifold 210 so as to be inserted into the pouch assemblies 212A-212F as the manifold 210 moves in a −Z direction toward the pouch assemblies 212. In the embodiments illustrated in FIGS. 2A and 2B, the manifold 210 is in a first position where the probes 214 are in a first position spaced from the pouch assemblies 212. The manifold 210 may move to a second position where the probes 214 are located in the pouch assemblies 212.

Reference is made to the pouch assembly 212A, which may be identical or substantially similar to all the pouch assemblies 212. The pouch assembly 212A may include a container 220 that stores the calibration reagent (not shown). Container 220 may be foil sided. A fitment device 222 may be sealed to the container 220. The fitment device 222 may secure the pouch assembly 212A to a cartridge chassis 224 within the reagent cartridge 106, as will be described in greater detail below. A probe 214A may be received within the fitment device 222 to access the calibration reagent stored in the container 220. For example, the manifold 210 may move from the first position to the second position, which may move the probe 214A into the fitment device 222 where the probe 214A moves a plug (not shown in FIGS. 2A and 2B) located within the fitment device 222.

Figure 3:
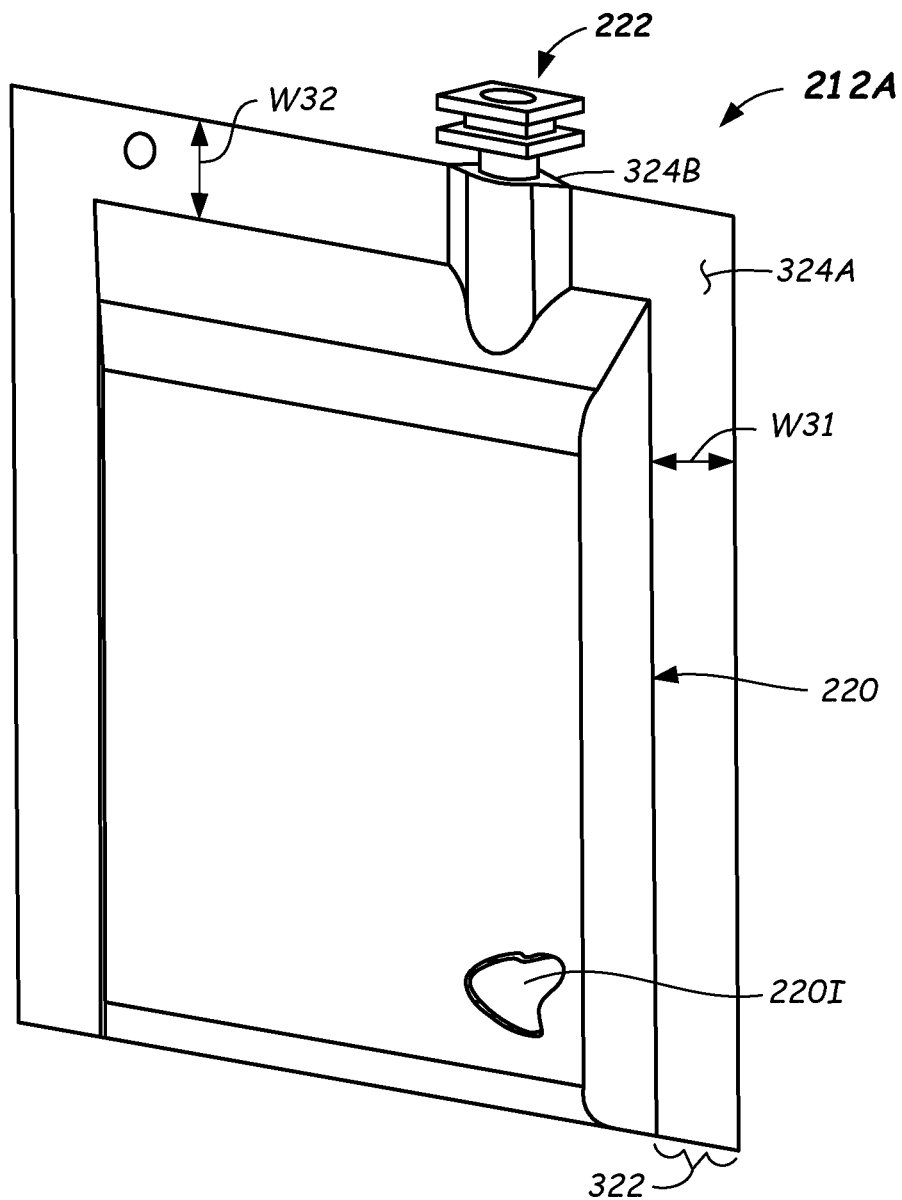
FIG. 3 illustrates a side isometric view of a pouch assembly including a fitment device that is configured to be used in a calibration cartridge according to embodiments disclosed herein.

Additional reference is now made to FIG. 3, which illustrates a front isometric view of the pouch assembly 212A removed from the reagent cartridge 106 (FIG. 2A). The rear view is substantially a mirror view of the front view. The container 220 may include a seam 322 extending around a least a portion of the periphery of the container 220.

The seam 322 forms a seal that prevents the calibration reagent from leaking from the container 220. The seam 322 may also prevent gases from entering and/or exiting the container 220, which could contaminate the calibration reagent. The seam 322 may have a width W31 on the sides of the container 220 and a width W32 on a top of the container 220 proximate the fitment device 222. The container 220 may be formed from a first container material 324A on the front and a second container material 324B on the rear that are adhered together at the seam 322. For example, the first container material 324A and the second container material 324B may foil-containing sheets that are heat-sealed together. The first container material 324A and the second container material 324B may include a foil layer (not shown) that has low gas permeability. For example, the foil layer may have a gas permeability of oxygen less than 1.2 $(cm^3)$ (mil)/(24 hrs) $(100 \text{ in}^2)$ (ATM) at 25° C. In some embodiments, the container 220 may be formed from a single piece of material that is folded at the bottom and sealed at the seam 322.

As described above, pouch assembly 212A includes the fitment device 222 that enables the probe 214A (FIG. 2A) to access the container 220 of reagent. The fitment device 222 may also secure the pouch assembly 212A within the reagent cartridge 106 (FIG. 2A). In the embodiment of FIG. 3, the first container material 324A and the second container material 324B may be sealed to opposite sides of the fitment device 222 at the seam so as to seal the container 220 to the fitment device 222. For example, the sealing of the first container material 324A to a first side of the fitment device 222 and the second container material 324B to a second side of the fitment device 222 may prevent the exchange of gases between the ambient environment and the interior of the container 220.

Figure 4:
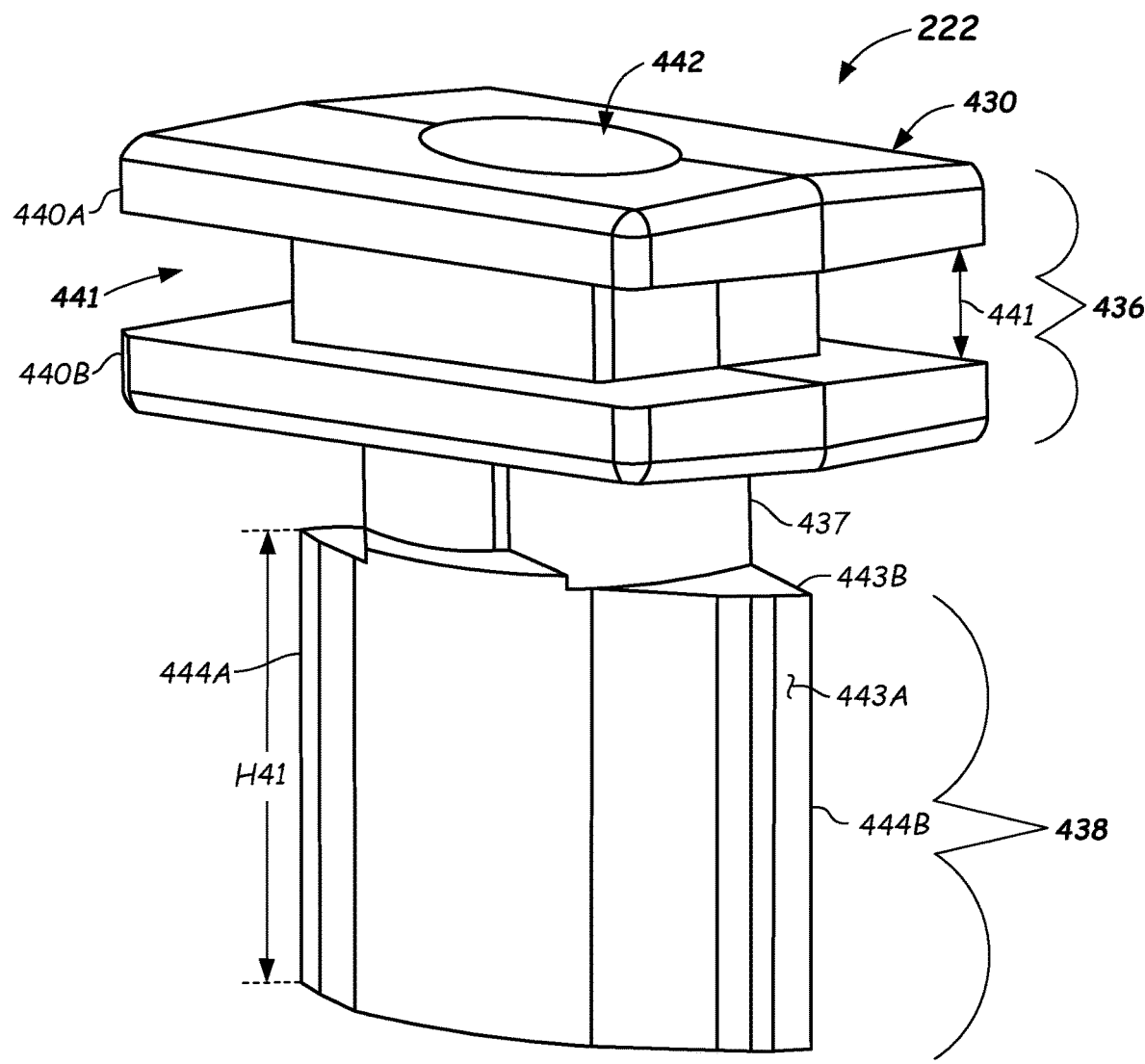
FIG. 4 illustrates an isometric view of a fitment device used in a reagent pouch assembly according to embodiments disclosed herein.

Reference is now made to FIG. 4, which illustrates a front isometric view of the fitment device 222. The fitment device 222 may include a core 430 that may comprise a first material. In some embodiments, the core 430 may comprise a single first material. In some embodiments, the first material of the core 430 may include a rigid material, such as nylon. In some embodiments, the first material of the core 430 may have a permeability of oxygen less than 9.5 $(cm^3)$ (mil)/(24 hrs) $(100 \text{ in}^2)$ (ATM) at 25° C. In some embodiments, the first material of the core 430 may even have a permeability of oxygen less than 1.2 $(cm^3)$ (mil)/(24 hrs) $(100 \text{ in}^2)$ (ATM) at 25° C. The low permeability of the first material of the core 430 may serve to prevent or significantly limit the permeation or transfer of gas, such as oxygen, through the core 430. Accordingly, the core 430 serves to prevent or significantly limit the degradation of the calibration reagents stored in the interior 221 (shown as a cutout) of the container 220 (FIG. 3).

The core 430 may include a securing portion 436 and a container portion 438, which may be located at respective ends of the core 430. An extension 437 may join the securing portion 436 and the container portion 438, although extension 437 may be optional. The securing portion 436 may include a first flange 440A and a second flange 440B separated by a distance D41 and thus forming a space 441 there between. The first flange 440A and the second flange 440B may secure the pouch assembly 212A to the cartridge chassis 224 (FIG. 2A). For example, the space 441 may receive a member of the cartridge chassis 224. The securing portion 436 may further include a first end of an aperture 442 that extends through the core 430. The aperture 442 may extend through the core 430 to the second end at the container portion 438.

The container portion 438 may include a first surface 443A and an opposite second surface 443B that join at a first end 444A and a second end 444B. Thus, the first container material 324A (FIG. 3) passes over and is sealed to the first surface 443A. The second container material 324B (FIG. 3) passes over and is sealed to the second surface 443B. The seam 322 (FIG. 3) between the first container material 324A and the second container material 324B may separate at the first end 444A and at the second end 444B to contact the fitment device 222 along its width.

As shown in FIG. 4, the first surface 443A and the second surface 443B may be curved. The curved first surface 443A and the curved second surface 443B enable the container portion 438 to have thickness, so the aperture 442 may pass through the container portion 438. The curve of the first surface 443A and the second surface 443B may also enable the first container material 324A and the second container material 324B to adhere to the container portion 438 without wrapping around any edges. The container portion 438 may have a height H41 that may be about the same distance as the width W32 (FIG. 3) of the seam 322. Although not all of the height H41 needs to be covered with the seam 322.

The first surface 443A may be identical or substantially similar to the second surface 443B. The first surface 443A and the second surface 443B may include a coating (not shown in FIG. 4) that adheres the first container material 324A and the second container material 324B to the first surface 443A and the second surface 443B. In some embodiments, the coating may be a heat sealable material, such as polypropylene. Other suitable heat sealable coatings or other sealable coating materials may be used.

Figure 5A:
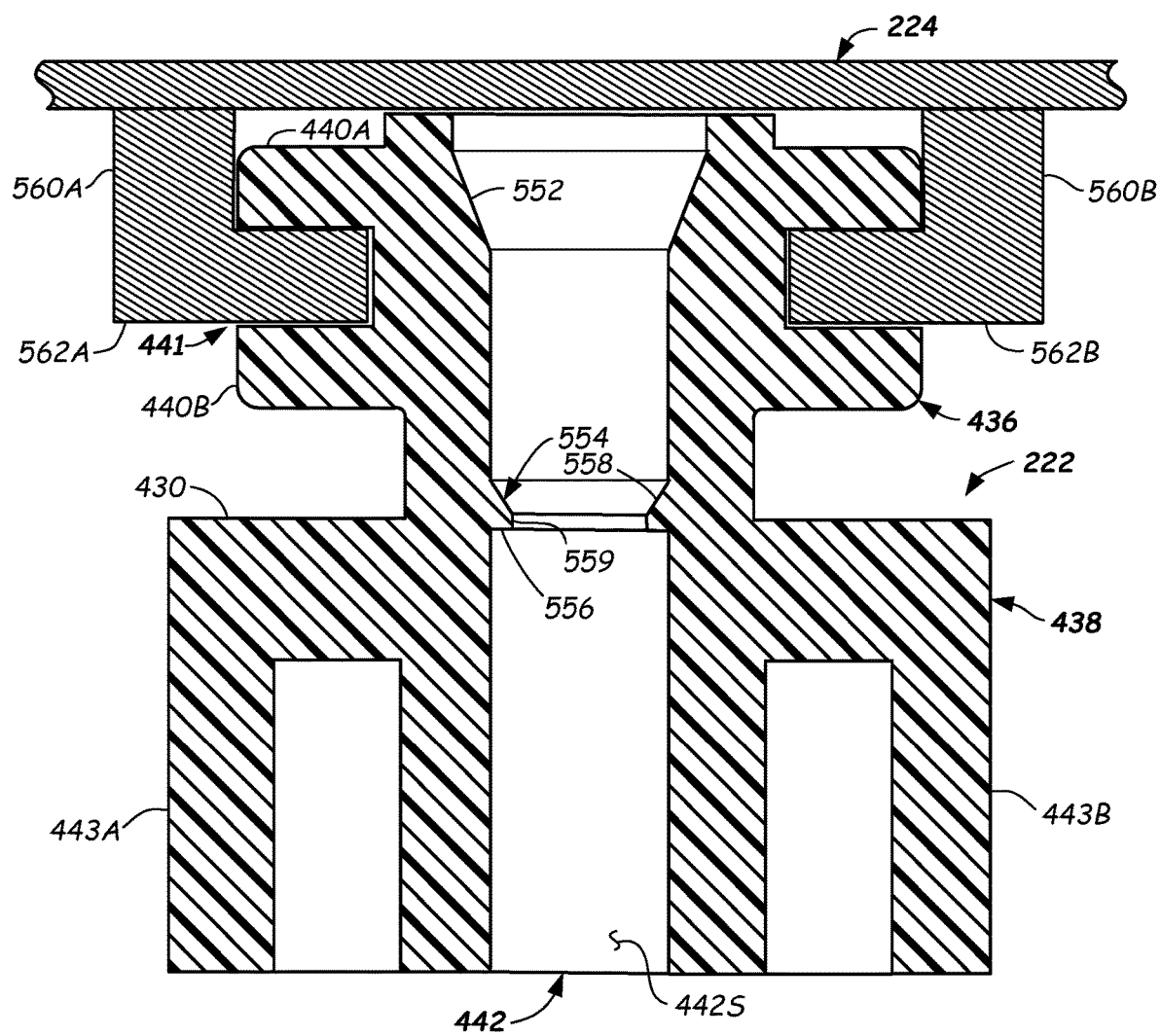
FIG. 5A illustrates a cross-sectioned side view of a fitment device including an aperture, wherein the aperture is devoid of a probe and a plug and wherein the fitment device is shown coupled to a chassis of a reagent cartridge according to embodiments disclosed herein.
Figure 5B:
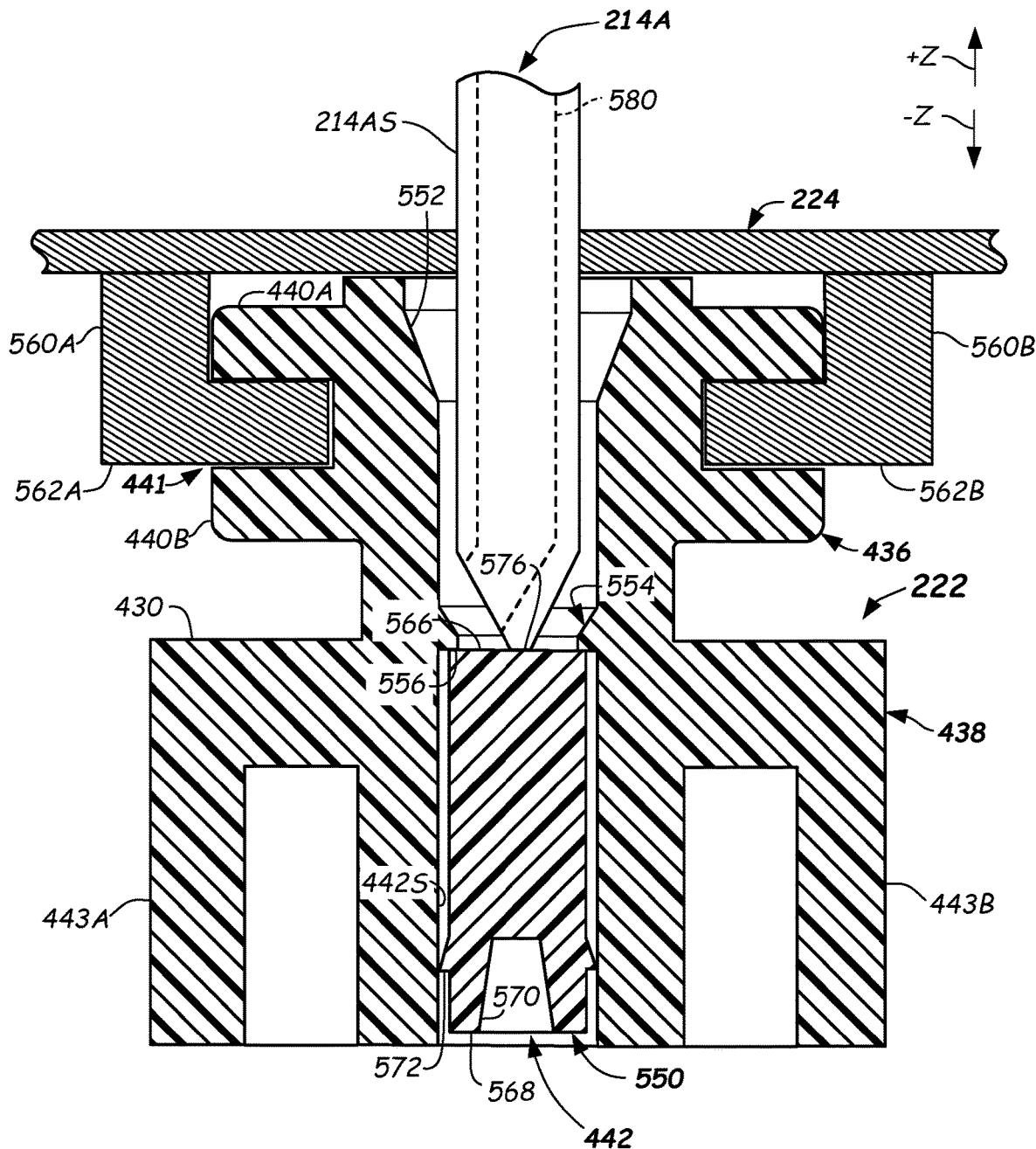
FIG. 5B illustrates a cross-sectioned side view of a fitment device of a pouch assembly wherein a probe of a reagent cartridge is shown in a second position and a plug in a first position within an aperture according to embodiments disclosed herein.
Figure 5C:
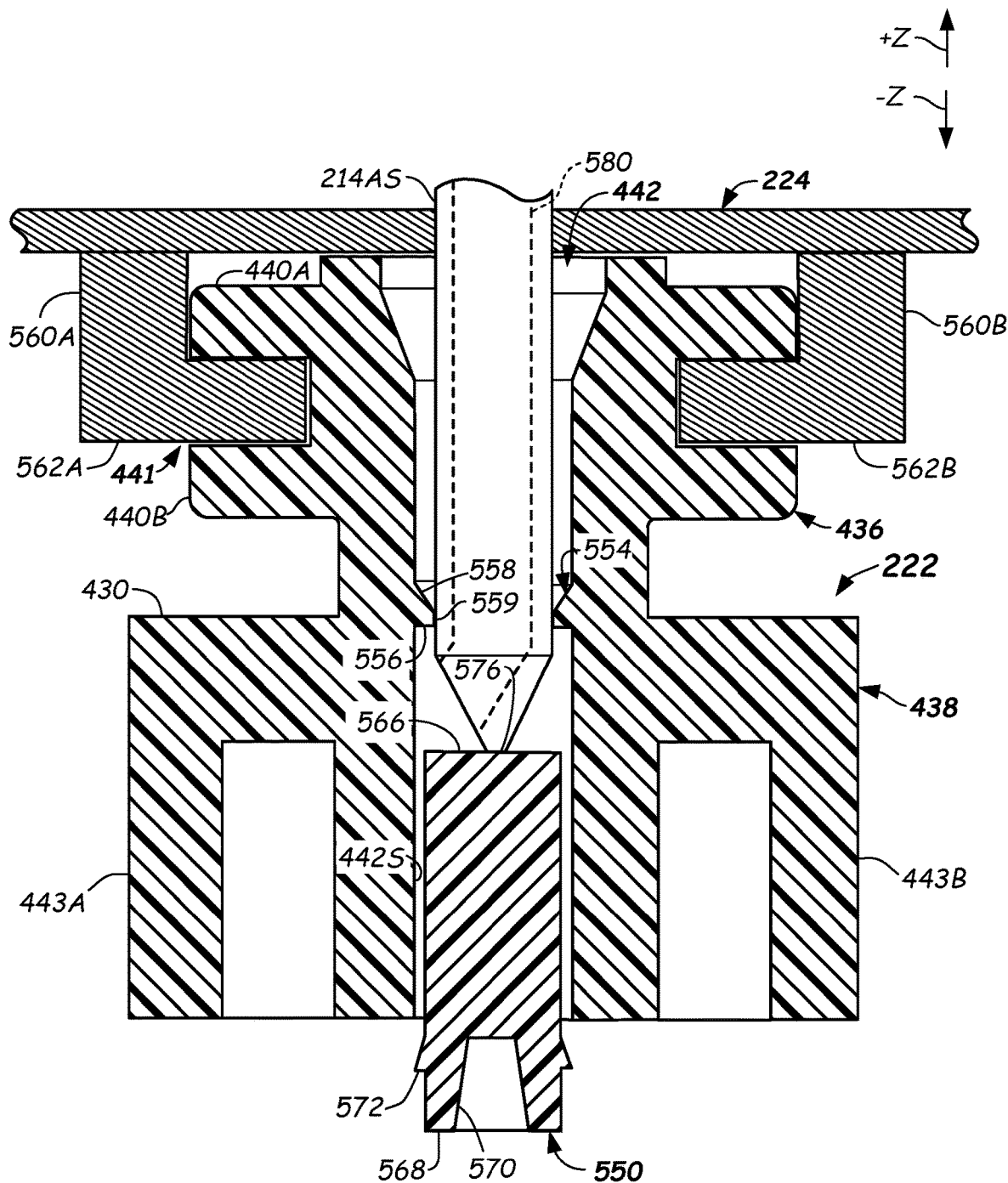
FIG. 5C illustrates a cross-sectioned side view of a fitment device of a pouch assembly including a probe of a reagent cartridge shown in a second position and a plug being pushed to transition the plug to a second position external to an aperture according to embodiments disclosed herein.

Additional reference is made to FIGS. 5A, 5B, and 5C. FIG. 5A illustrates a cross-sectioned side view of the fitment device 222 wherein the aperture 442 is devoid of the probe 214A (FIG. 2A) and a plug (550—FIGS. 5B and 5C). FIG. 5B illustrates a cross-sectioned view of the fitment device 222 with the probe 214A inserted within the aperture 442 and the plug 550 located in a first position within the aperture 442. FIG. 5C illustrates a cross-sectioned side view of the fitment device 222 with the probe 214A inserted in the aperture 442 at a second position. At the second position, the plug 550 is moved sufficiently to open a passageway through the aperture 442. The probe 214A may continue to move the plug 550 until the plug 550 is removed from the aperture 442 and is pushed into the container interior 2201. Although the plug 550 may be retained in the aperture in some embodiments so long as a sufficient passage way is provided to access the reagent contained in the container interior 2201.

In some embodiments, the aperture 442 may include a conical portion 552 in an upper portion thereof. The conical portion 552 may guide the probe 214A into the aperture 442 as the probe 214A transitions from the first position spaced away from the aperture 442 to the second position where the probe 214A is located within the aperture 442 as shown in FIGS. 5B and 5C. The conical portion 552 may have a wide diameter proximate the first end of the aperture 442 and a narrowing diameter away from the first end of the aperture 442.

The aperture 442 may further include a lip 554 that extends into the aperture 442. In some embodiments, the lip 554 may be annular and may extend around the circumference of the aperture 442. The lip 554 may include a contact surface 556 that contacts the plug 550 (FIG. 5B) and limits the movement of the plug 550 in a +Z direction as described below. The lip 554 may include an inclined surface 558 on an upper portion that may serve to guide the probe 214A within the aperture 442 past the lip 554. In addition, the lip 554 may include a sealing surface 559 that is configured to contact (e.g., seal to) the exterior surface 214AS of the probe 214A. The sealing surface 559 may be a cylindrical surface and a diameter of the sealing surface 559 may be slightly smaller than an outside diameter of the exterior surface 214AS of the probe 214A. Other suitable seal types may be used, such as lip seals.

As described above, the sealing surface 559 may seal to an exterior surface 214AS of the probe 214A when the probe 214A is located within the aperture 442. The seal between the sealing surface 559 and the exterior surface 214AS of the probe 214A prevents or reduces the exchange of gases between the container interior 2201 of the container 220 (FIG. 3) and the exterior of the container 220 when the probe 214A is located and sealed within the aperture 442. In some embodiments, the sealing surface 559 may be made of a material, such as a pliable material, that may seal against the exterior surface 212AS of the probe 214A. The seal may be a separate component retained in a groove formed in the aperture 442 in some embodiments. In some embodiments, the sealing surface 559 may be the same material (e.g., nylon) as the core 430.

The cartridge chassis 224 may include members extending from a lower surface that coupled to and support the fitment device 222 and thus the pouch assembly 212A. In the embodiment depicted in FIGS. 5A-5C, the cartridge chassis 224 includes a first member 560A and a second member 560B that extend from the cartridge chassis 224. The first member 560A includes a first extension 562A and the second member 560B includes a second extension 562B that may be received in the space 441. For example, the first extension 562A and the second extension 562B may be received in the space 441 so as to secure the fitment device 222 and the pouch assembly 212A to the cartridge chassis 224.

Reference is now made to FIG. 5B, which illustrates the fitment device 222 with the probe 214A and the plug 550 located within the aperture 442. The plug 550 may be located in the container portion 438 of the fitment device 222. Accordingly, the plug 550 may be proximate the location of the seam 332 (FIG. 3), which further prevents gases from permeating by way of the seam 332. As shown, the probe 214A has moved from the first position removed from the aperture 442 to a second position within the aperture 442, and is shown in contact with the plug 550. The plug 550 is in the first position within the aperture 442. The plug 550 may include a first end 566 having a surface (e.g., a top surface) that may contact the contact surface 556 of the lip 554 when the plug 550 is in the first position. The lip 554 may limit movement of the plug 550 in the +Z direction. In some embodiments, the plug 550 comprises a material with very low gas (e.g., oxygen) permeability, such as polyethylene terephthalate (PET). In some embodiments, the plug 550 has a permeability of oxygen that is less than 10 $(cm^3)$ (mil)/(24 hrs) (100 $in^2$) (ATM) at 25° C. The plug 550 may be made of other materials that can have low oxygen permeability, such as less than 10 $(cm^3)$ (mil)/(24 hrs) (100 $in^2$) (ATM) at 25° C.

The plug 550 may include a second end 568 that may be fluted. The second end 568 may include an annular ring 570 formed by an opening in the second end 568, which may provide flexibility in the second end 568 of the plug 550. An annular tab 572 (e.g., a sealing portion) may extend from the annular ring 570 and may contact a sealing surface 442S of the aperture 442. The contact between the annular tab 572 and the sealing surface 442S of the aperture 442 may create a seal that prevents the flow of gases through the aperture 442, i.e. blocks the aperture 442. Thus, gases may be prevented from interfering with a calibration reagent stored in the container interior 2201 of the container 220 (FIG. 3) sealed to the fitment device 222. The annular tab 572 may have a diameter that is slightly greater than a diameter of the aperture 442, for example. Flex provided by the annular ring 570 may enable the plug 550 to be inserted into the aperture 442 and provide a frictional force that is great enough to retain the plug within the aperture 442.

The probe 214A may include an end 576 that contacts the first end 566 of the plug 550 as the probe 214A moves in the −Z direction. As illustrated in FIG. 5C, as the probe 214A moves in the −Z direction, the probe 214A pushes the plug 550 in the −Z direction. Eventually, the annular tab 572 is released from the aperture 442 and the plug 550 may fall into the container 220 (FIG. 3). The exterior surface 214AS of the probe 214A may seal against the sealing surface 559 (FIG. 5A) to prevent gases from exchanging with the container interior 2201 (FIG. 3). The probe 214A may include a passage 580 extending through the probe 214A. The passage 580 may couple to the tube 215 (FIG. 2A) in the manifold 210. The passage 580 may transfer the contents of the container interior 2201 (FIG. 3) to devices (not shown) in the gas analyzer 100 (FIG. 1A) for analysis thereof.

The core 430 may be formed by an injection molding process. For example, nylon or another suitably low gas permeable material may be injected into a mold to form the core 430. The plug 550 may be formed from a material also having low gas permeability, such as PET. In some embodiments, the plug 550 may be formed by an injection mold process. The plug 550 may be inserted into the aperture 442 by way of the second end proximate the container portion 438 prior to sealing the container 220 to the fitment device 222. The plug 550 may be pressed into the aperture 442 until the first end 566 of the plug 550 contacts the contact surface 556 of the lip 554. At this point, the annular tab 572 forms a seal with the surface 442S of the aperture 442. Friction between the annular tab 572 and the surface 442S of the aperture 442 may retain the plug 550 within the aperture 442.

The container 220 (FIG. 3) may be adhered to the container portion 438 of the fitment device 222. For example, the first container material 324A may be adhered to the first surface 443A of the fitment device 222 and the second container material 324B may be adhered to the second surface 443B. All of the core 430, the container 220, and the plug 550 may be made from low gas permeable materials, which prevent the exchange of gases between the interior and exterior of the container 220, such as having a low oxygen permeability of less than 10 $(cm^3)$ (mil)/(24 hrs) (100 $in^2$) (ATM) at 25° C. Based on the foregoing, gas permeation of the pouch assembly 212A is very low, which increases the shelf life of the contents stored in the pouch assembly 212A.

The securing portion 436 of the fitment device 222 may be secured to the cartridge chassis 224 by way of the first member 560A and the second member 560B. For example, the first extension 562A and the second extension 562B may be received in the space 441. During operation, the manifold 210 (FIG. 2A) to which the probes 214 are attached may be moved from a first position where the probes 214 are spaced from the fitment devices to a second position where the probes 214 are received in the fitment devices 222. As shown in FIG. 5C, the probe 214A moves in the −Z direction into the aperture 442 where the probe 214A contacts the plug 550. As the probe 214A continues to move, the probe 214A can push the plug 550 from the aperture 442 where it may fall into the container interior 2201 of the container 220 (FIG. 3). The contents of the container 220 may be sampled by way of the passage 580 and the tube 215 and analyzed by the gas analyzer 100. The gas analyzer 100 may then be calibrated based on the analysis test results.

Figure 6:
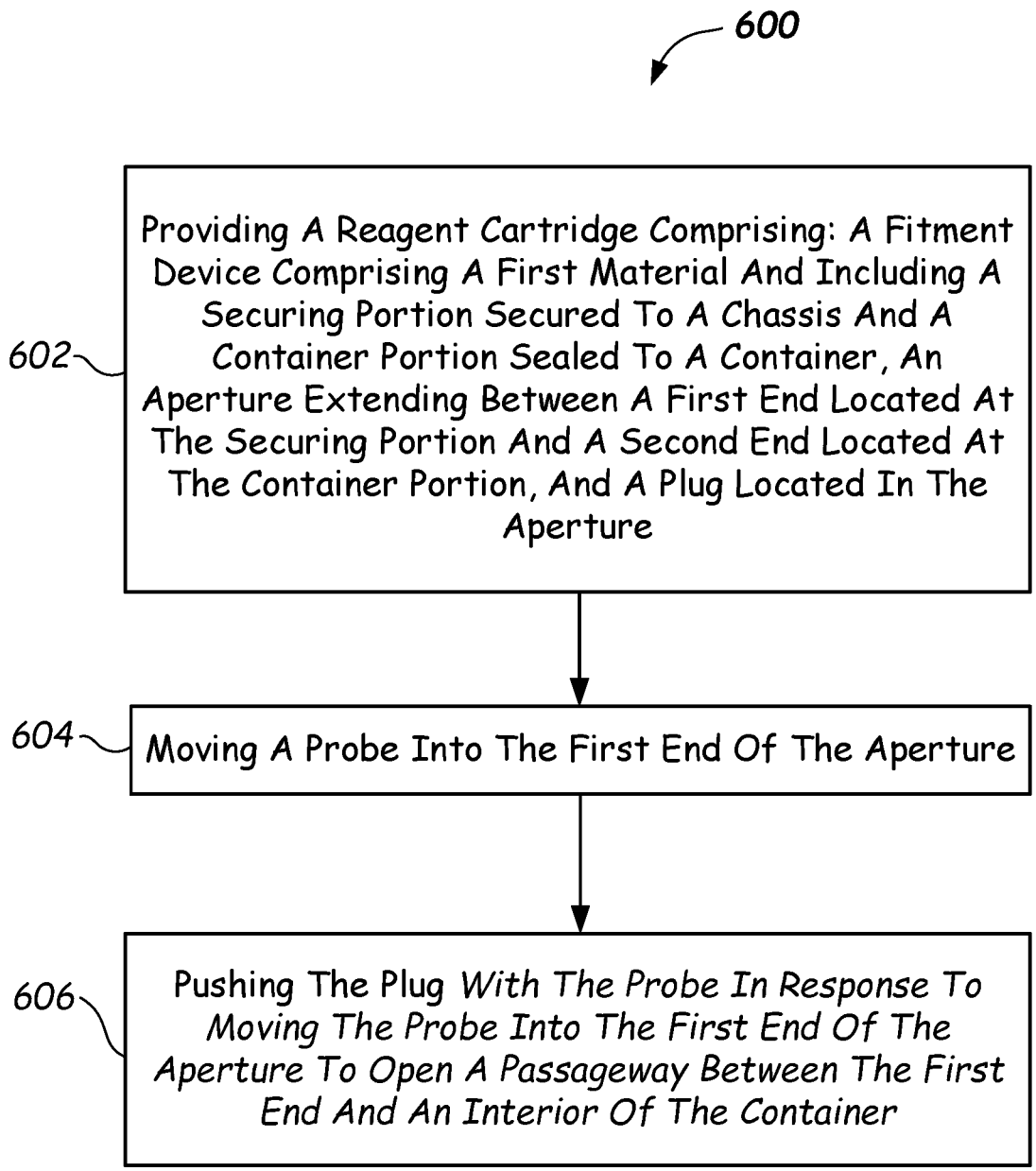
FIG. 6 illustrates a method of using a reagent cartridge according to embodiments disclosed herein.

In another aspect, a method 600 of using a reagent cartridge is provided and illustrated by the flowchart of FIG. 6. The method 600 may include, at 602, providing a reagent cartridge (e.g., reagent cartridge 106) comprising: a fitment device (e.g., fitment device 222) comprising a first material and including a securing portion (e.g., securing portion 436) secured to a chassis (e.g., cartridge chassis 224) and a container portion (e.g., container portion 438) sealed to a container (e.g., container 220), an aperture (e.g., aperture 442) extending between a first end located at the securing portion and a second end located at the container portion, and a plug (e.g., plug 550) located in the aperture, the plug comprising a second material. The second material can be different than the first material. The method 600 may include, at 604, moving a probe into the first end of the aperture. The method may include, at 606, pushing the plug out of the second end of the aperture with the probe in response to moving the probe into the first end of the aperture to open a passageway between the first end and an interior of the container.

It should be readily appreciated that the present disclosure is susceptible of broad utility and application. Many embodiments and adaptations of the present disclosure other than those herein described, as well as many variations, modifications, and equivalent arrangements, will be apparent from, or reasonably suggested by, the present disclosure and the foregoing description thereof, without departing from the substance or scope of the present disclosure. Accordingly, while the present disclosure has been described herein in detail in relation to specific embodiments, it is to be understood that this disclosure is only illustrative and presents examples of the present disclosure and is made merely for purposes of providing a full and enabling disclosure. This disclosure is not intended to be limited to the particular apparatus, assemblies, systems, and/or methods disclosed, but, to the contrary, the intention is to cover all modifications, equivalents, and alternatives falling within the scope of the claims.

Illustrative Embodiments

1. A reagent cartridge, comprising:
    at least one pouch assembly configured to hold a reagent, the at least one pouch assembly further comprising:
        a fitment device comprising a first material and including a securing portion configured to secure to a chassis and a container portion sealed to a container of the pouch assembly,
        an aperture including a first end located at the securing portion and a second end located at the container portion, and
        a plug located in the aperture; and
    at least one probe having a first position where the at least one probe is spaced from the first end of the aperture and a second position where the at least one probe is received in the first end of the aperture, wherein the at least one probe is configured to move the plug in the aperture in response to the at least one probe being in the second position to open a passageway between the first end and the container.

2. The reagent cartridge of claim 1, further comprising a manifold, wherein the at least one probe is coupled to the manifold, and wherein the manifold includes a tube coupled to the at least one probe.

3. The reagent cartridge of claim 2, wherein the manifold is moveable between:
    a first position wherein the at least one probe is in the first position, and
    a second position wherein the at least one probe is located in the second position.

What is claimed is:
1. A fitment device, comprising:
    a core comprising a first material and including a securing portion configured to secure to a chassis and a container portion configured to seal to a container, wherein the first material is coextensive from a first end of the core to a second end of the core and forms a solid sidewall between the first and second ends of the core and thus prevents or significantly limits the permeation or transfer of gas through the core;
    an aperture that forms a sealable passageway that extends through the core, the aperture comprising a first end located at the securing portion and a second end located at the container portion, the aperture configured to receive a probe in the first end; and
    a plug located in the aperture, wherein the plug is movable in the aperture upon contact with the probe to open the passageway between the first end and the second end, wherein the plug includes an annular tab extending from an exterior surface of the plug, and wherein the annular tab frictionally engages a surface of the aperture and creates a releasable seal that prevents or reduces the flow of gases through the aperture.

2. The fitment device of claim 1, wherein the plug comprises a second material that is different than the first material.

3. The fitment device of claim 1, wherein the core comprises nylon.

4. The fitment device of claim 1, wherein the plug comprises polyethylene terephthalate (PET).

5. The fitment device of claim 1, wherein the plug has a permeability of oxygen that is less than 10 $(cm^3)(mil)/(24\ hrs)(100\ in^2)(ATM)$ at 25° C.

6. The fitment device of claim 1, wherein the aperture includes a lip, wherein the lip is configured to limit movement of the plug in a direction toward the first end of the aperture, and wherein the lip includes a sealing surface configured to frictionally engage at least a portion of an exterior surface of the probe when the probe is located within the aperture to form a releasable seal between the sealing surface and the exterior surface of the probe.

7. The fitment device of claim 1, further comprising a container sealed to the container portion, wherein the second end of the aperture is located in the container.

8. The fitment device of claim 6, wherein the sealing surface has a diameter that is smaller than an outside diameter of at least a portion of the exterior surface of the probe.

9. The fitment device of claim 6, wherein the sealing surface is formed of a pliable material that is separate from the material from which the rest of the aperture is formed.

10. The fitment device of claim 6, wherein the sealing surface is a separate component retained in a groove formed in the aperture.

11. A pouch assembly, comprising:
a container; and
a fitment device coupled to the container, the fitment device further comprising:
- a core comprising a first material and including a securing portion configured to secure to a chassis, and a container portion configured to seal to the container, wherein the first material is coextensive from a first end of the core to a second end of the core and forms a solid sidewall between the first and second ends of the core and thus prevents or significantly limits the permeation or transfer of gas through the core;
- an aperture that forms a sealable passageway that extends through the core, the aperture comprising a first end located at the securing portion and a second end located at the container portion, the aperture configured to receive a probe in the first end; and
- a plug located in the aperture, wherein the plug is movable in the aperture upon contact with the probe to open the passageway between the first end and the container, wherein the plug includes an annular tab extending from an exterior surface of the plug, and wherein the annular tab frictionally engages a surface of the aperture and creates a releasable seal that prevents or reduces the flow of gases through the aperture.

12. The pouch assembly of claim 11, wherein the plug comprises a second material that is different than the first material.

13. The pouch assembly of claim 11, wherein the plug has a permeability of oxygen that is less than 10 (cm$^3$) (mil)/(24 hrs)(100 in$^2$)(ATM) at 25° C.

14. The pouch assembly of claim 11, wherein the aperture includes a lip, wherein the lip is configured to limit movement of the plug in a direction toward the first end, and wherein the lip includes a sealing surface configured to frictionally engage at least a portion of an exterior surface of a probe when the probe is located within the aperture to form a releasable seal between the sealing surface and the exterior surface of the probe.

15. The pouch assembly of claim 11, wherein the second end of the aperture is located in the container.

16. The pouch assembly of claim 14, wherein the sealing surface has a diameter that is smaller than an outside diameter of at least a portion of the exterior surface of the probe.

17. The pouch assembly of claim 14, wherein the sealing surface is formed of a pliable material that is separate from the material from which the rest of the aperture is formed.

18. The pouch assembly of claim 14, wherein the sealing surface is a separate component retained in a groove formed in the aperture.

19. A reagent cartridge configured for insertion in a gas analyzer, the reagent cartridge comprising:
the pouch assembly of claim 11; and
at least one probe having a first position in which the at least one probe is spaced from the first end of the aperture and a second position in which the at least one probe is received in the first end of the aperture, wherein the at least one probe is configured to move the plug in the aperture in response to the at least one probe being in the second position to open a passageway between the first end and the container.

20. A method of using a reagent cartridge, comprising:
providing a reagent cartridge comprising:
- a fitment device comprising a first material and including a securing portion secured to a chassis and a container portion sealed to a container, wherein the first material is coextensive from a first end of the core to a second end of the core and forms a solid sidewall between the first and second ends of the core and thus prevents or significantly limits the permeation or transfer of gas through the core,
- an aperture forming a sealable passageway that extends between a first end located at the securing portion and a second end located at the container portion, and
- a plug located in the aperture, wherein the plug includes an annular tab extending from an exterior surface of the plug, and wherein the annular tab frictionally engages a surface of the aperture and creates a releasable seal that prevents or reduces the flow of gases through the aperture;

moving a probe into the first end of the aperture; and
pushing the plug with the probe in response to moving the probe into the first end of the aperture to open the passageway between the first end and an interior of the container.

21. The method of claim 20, further comprising sealing the probe against a surface of the aperture.

* * * * *